(12) United States Patent
Scheiner et al.

(10) Patent No.: US 6,415,183 B1
(45) Date of Patent: Jul. 2, 2002

(54) METHOD AND APPARATUS FOR DIAPHRAGMATIC PACING

(75) Inventors: Avram Scheiner, Vadnais Heights; Veerichetty Kadhiresan, Lino Lakes, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/456,879

(22) Filed: Dec. 9, 1999

(51) Int. Cl.[7] .................................................. A61N 1/36
(52) U.S. Cl. ............................................. 607/42; 607/9
(58) Field of Search ....................................... 607/9, 42

(56) References Cited

U.S. PATENT DOCUMENTS

| | | | |
|---|---|---|---|
| 3,896,817 A | 7/1975 | Hursen et al. | 128/419 R |
| 4,827,935 A | 5/1989 | Geddes et al. | 128/419 |
| 4,830,008 A | 5/1989 | Meer | 128/421 |
| 5,199,428 A | 4/1993 | Obel et al. | 128/419 C |
| 5,300,094 A | 4/1994 | Kallok et al. | 607/42 |
| 5,540,733 A | 7/1996 | Testerman et al. | 607/42 |
| 5,792,208 A | 8/1998 | Gray | 607/36 |
| 5,836,976 A | 11/1998 | Min et al. | 607/6 |
| 6,006,134 A | * 12/1999 | Hill et al. | |

FOREIGN PATENT DOCUMENTS

| | | | |
|---|---|---|---|
| EP | 0940155 | 2/1998 | A61N/1/36 |
| FR | 2305168 | 10/1976 | A61H/31/00 |

* cited by examiner

Primary Examiner—Scott M. Getzow
(74) Attorney, Agent, or Firm—Schwegman, Lundberg, Woessner & Kluth, P.A.

(57) ABSTRACT

A diaphragmatic pacing system and method. The method includes monitoring a signal representing a patient's respiratory activity, and delivering an electric stimulus from a lead to the phrenic nerve when the signal indicates that the respiratory activity is below a predetermined level. Physiological state information, such as the respiration activity or minute ventilation, is sensed using the implanted lead and the method delivers an output based on such input. Another embodiment provides concurrent sensing and pacing of heart and diaphragm using a single implanted pulse generator. The implantable system includes at least one lead and a signal processing circuit coupled to the lead. The signal processing circuit processes a signal representative of a respiratory activity. A controller coupled to the signal processing circuit analyzes the signal and when the signal indicates a need for respiratory therapy the controller outputs a controller signal. An output circuit coupled to the controller, for delivering a pulse in response to the controller signal, the pulse having an amplitude high enough to stimulate a phrenic nerve.

36 Claims, 10 Drawing Sheets

METHOD AND APPARATUS FOR DIAPHRAGMATIC PACING

FIELD OF THE INVENTION

The present invention relates generally to implantable medical devices, and more specifically to an apparatus and method for treating breathing disorders.

BACKGROUND

When properly functioning, the diaphragm maintains a respiration rate of about 10–50 breaths per minute. A variety of ailments can cause a person not to breathe properly. One such disorder is central sleep apnea, which occurs when the brain fails to send the appropriate message to the muscles responsible for initiating the respiratory cycle. This causes brief interruptions of breathing during sleep. Treatment of central sleep apnea is important because it may be associated with irregular heartbeat, high blood pressure, heart attack, and stroke.

Another breathing disorder is Cheyne-Stokes respiration, which is characterized by a cycle of rapid, deep breathing followed by apneic episodes. Other patients suffer from intractable hiccups, which are chronic and uncontrollable. Also, there are many respiratory problems which are related to patients who have paralysis and are unable to breath on their own.

One method of treating such respiratory problems is phrenic nerve pacing, which is also called diaphragmatic pacing. The phrenic nerve is generally known as the motor nerve of the diaphragm. It runs through the thorax, along the heart, and then to the diaphragm. Diaphragmatic pacing is the use of electronic stimulation of the phrenic nerve to control the patient's diaphragm and induce a respiratory cycle. In the past, this has been accomplished by surgically placing a nerve cuff on the phrenic nerve, and then delivering an electric stimulus. The electric stimulus of the phrenic nerve then causes the diaphragm to induce a respiratory cycle. One problem associated with this method is that nerve cuff surgery can be quite invasive and it runs the risk of nerve damage. Another problem with the phrenic nerve cuff method is that nerve cuffs are a relatively undeveloped technology.

Another problem facing respiratory patients is that many also suffer from heart problems which require heart pacing. If the patient chooses to receive diaphragmatic pacing therapy and heart pacing therapy, the patient is required to have two independent stimulation systems implanted in their bodies. This increases the risk of complications both during and after surgery.

Thus, there is a need for a system which provides reliable and safe phrenic nerve pacing, and also permits a physician to incorporate heart pace management and diaphragmatic pace management into a single implantable pace management system.

SUMMARY

The present system provides a method and apparatus for performing diaphragmatic pacing. In one embodiment, a pacing lead is situated in or near a patient's heart so that the electrode on the lead is situated to deliver an electric stimulus to the patient's phrenic nerve when the need for it is determined by a controller.

In further embodiments, the present system is applicable for treating respiratory ailments such as sleep apnea. The system provides for sensing a physiological state of the patient related to respiration effort using an electrode implanted in the heart. When a physiological state indicating a need for therapy is detected, an electrical stimulus is triggered by a controller, and the electrode delivers an electric stimulus to the phrenic nerve, initiating a respiratory cycle. In another embodiment, when a physiological state indicating a respiratory event is detected, the controller inhibits delivery of an electrical stimulus, which is programmed to be delivered at a predetermined rate.

In a further embodiment, the system includes a system for pacing both the patient's diaphragm and their heart. This system includes inserting a lead into the patient's body so that an electrode is situated to stimulate both the heart and the phrenic nerve. Two different stimuli voltages are deliverable. A first at an amplitude which is higher than the cardiac stimulation threshold but lower than the diaphragm pacing threshold, and a second, more powerful, stimulus at a level which stimulates both the heart and diaphragm at the same time.

Some of the advantages of the present system are that it provides diaphragmatic pacing using the advanced, developed technology provided by modern cardiac pacing lead technology. It also provides phrenic pacing without the invasive surgery associated with attaching nerve cuffs. Furthermore, it provides concurrent heart pacing and diaphragm pacing using one implanted system instead of two.

DETAILED DESCRIPTION

In the following detailed description, reference is made to the accompanying drawings which form a part hereof, and in which is shown by way of illustration specific embodiments in which the system may be practiced. These embodiments are described in sufficient detail to enable those skilled in the art to practice the invention, and it is to be understood that the embodiments may be combined or that other embodiments may be utilized and that structural changes may be made without departing from the spirit and scope of the present invention. The following detailed description is, therefore, not to be taken in a limiting sense, and the scope of the present invention is defined by the appended claims and their equivalents.

DESCRIPTION OF THE SYSTEM

Figure 1B:
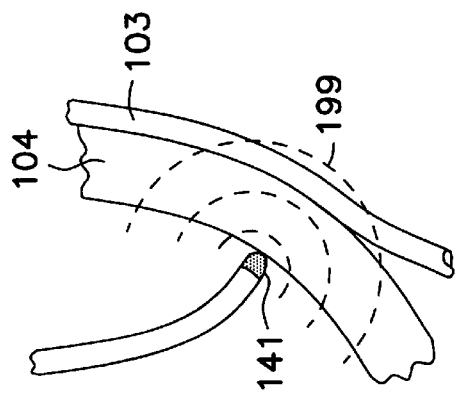
FIG. 1B is a cut-away view of a phrenic nerve being stimulated.
Figure 1A:
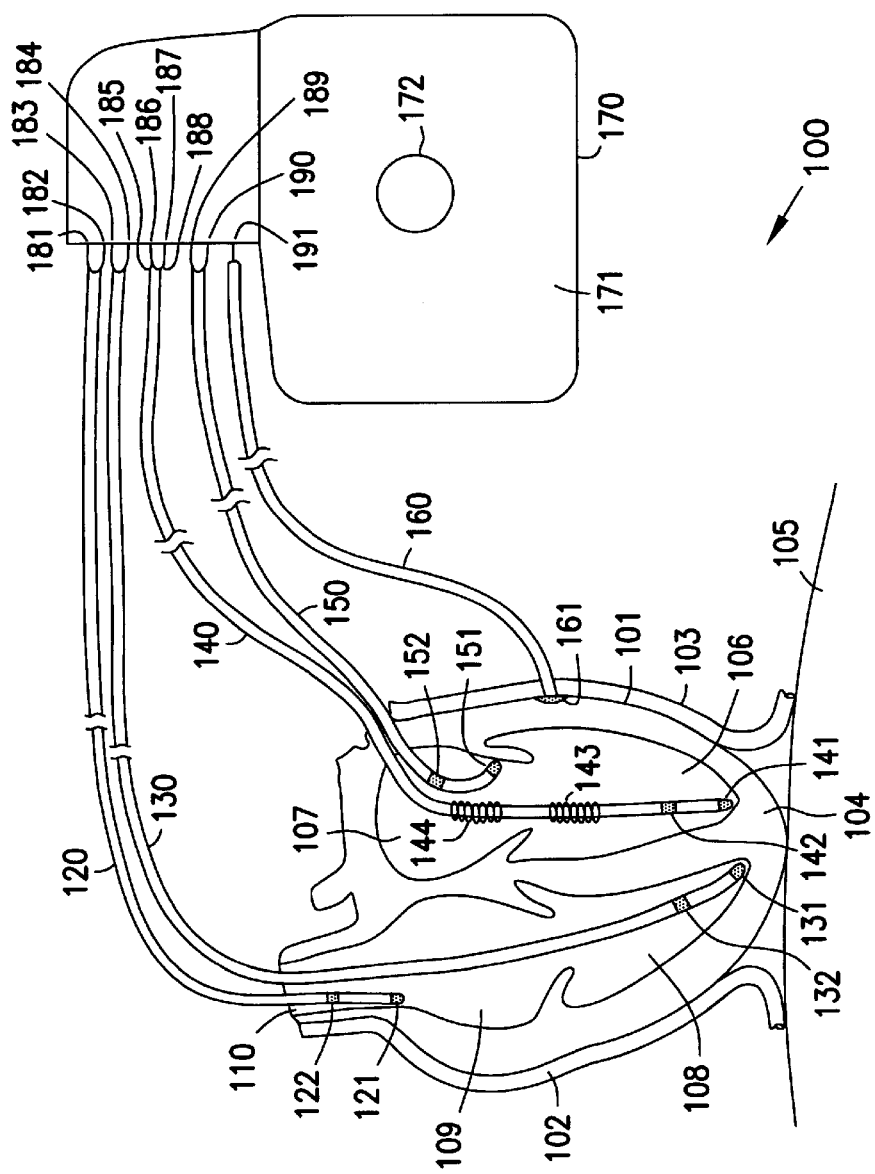
FIG. 1A is a view of a heart and the environment in which one embodiment of the present system is performed.

FIG. 1A shows one embodiment of a diaphragmatic pacing system 100 and an environment in which it is used. FIG. 1A is to be understood as an exemplary environment for the purpose of explaining the present system. Although system 100 is shown incorporating five leads, it is understood that some aspects of the system can be performed with only one lead and others with more than five leads. The system is shown having five leads merely as an aid for explaining the present system. The present system is not limited by the number of leads.

The present system is described in the context of a heart 101. Disposed on heart 101 is a phrenic nerve which branches into two sections, a right phrenic nerve 102 running along the medial side of heart 101 to a diaphragm 105, and a left phrenic nerve 103 running along the lateral side of heart 101 to diaphragm 105. Heart 101 also includes a superior vena cava 110, a right atrium 109, a right ventricle 108, a left atrium 107, a left ventricle 106, and a myocardium 104. It is noted that when either branch 102 or 103 of the phrenic nerve receives a high enough electric stimulus the phrenic nerve causes diaphragm 105 to contract, causing a respiratory cycle to begin.

System 100 includes a first lead 120. Lead 120 is a bipolar pacing lead having a tip electrode 121 and a ring electrode 122. Electrodes 121 and 122 of first lead 120 are disposed within superior vena cava 110 of heart 101. Electrodes 121 and 122 of first lead 120 are coupled to inputs 181 and 182 on a device 170. In this embodiment, lead 120 is a bipolar pacing lead. As will be explained below, in other embodiments of the present system first lead 120 can be a unipolar lead having a single electrode with an electrode on device 170 or another lead serving as the counter electrode. Tip electrode 121 and ring electrode 122 can be used for sensing respiratory activity by a method such as minute ventilation, as will be explained below, and/or for delivering diaphragm therapy by delivering an electric stimulus to phrenic nerve 102, as will be explained below.

System 100 further includes an exemplary second lead 130. Lead 130 is a bipolar pacing lead having a tip electrode 131 and a ring electrode 132. Electrodes 131 and 132 of second lead 130 are disposed within right ventricle 108 of heart 101. Electrodes 131 and 132 of lead 130 are coupled to inputs 183 and 184 on device 170. In this embodiment, lead 130 is a bipolar pacing lead. In other embodiments of the present system second lead 130 can be a unipolar lead having a single electrode with an electrode on device 170 or another lead serving as the counter electrode. Tip electrode 131 and ring electrode 132 can be used for sensing respiratory activity by a method such as minute ventilation, as will be explained below, and/or for sensing heart activity, and/or for delivering heart therapy such as pacing.

System 100 includes an exemplary third lead 140. Lead 140 is a defibrillation lead having a tip electrode 141, a ring electrode 142, a distal defibrillation coil electrode 143, and a proximate defibrillation coil electrode 144. Electrodes 141 and 142 of lead 140 are disposed within left ventricle 106 of heart 101. Distal defibrillation coil electrode 143 is disposed within left ventricle 106 and proximate defibrillation coil electrode 144 is disposed within left atrium 107. Electrodes 141–144 of third lead 140 are coupled to inputs 185–188 respectively on device 170. In this embodiment, lead 140 is a defibrillation lead. In other embodiments of the present system, lead 140 can be a bipolar lead or a unipolar lead. Tip electrode 141 and ring electrode 142 can be used for sensing respiratory activity, such as minute ventilation, or for sensing heart activity. The electrodes can also be used for delivering heart pacing therapy. They can also be used for delivering diaphragm therapy by stimulating phrenic nerve 103. Distal defibrillation coil electrode 143 and proximate defibrillation coil electrode 144 can be used for delivering a defibrillation countershock to heart 101.

System 100 further includes an exemplary fourth lead 150. Lead 150 is a bipolar pacing lead having a tip electrode 151 and a ring electrode 152. Electrodes 151 and 152 of lead 150 are disposed within left atrium 107 of heart 101. Electrodes 151 and 152 of lead 150 are coupled to inputs 189 and 190 on device 170. In this embodiment, lead 150 is a bipolar pacing lead. In other embodiments of the present system second lead 150 can be a unipolar lead having a single electrode. Tip electrode 151 and ring electrode 152 can be used for sensing respiratory activity by a method such as minute ventilation. They can also be used for sensing heart activity and/or for delivering heart therapy. The electrodes can also be used to deliver diaphragm therapy by stimulating phrenic nerve 103.

System 100 further includes an exemplary fifth lead 160. Lead 160 is a pacing lead having an epicardial tip electrode 161. Electrode 161 is attached to an epicardial portion of heart 101. Electrode 161 is coupled to input 191 on device 170. Electrode 161 can be used for sensing respiratory activity or heart activity and/or for delivering heart therapy or diaphragm therapy.

The exemplary environment and leads shown in FIG. 1A are shown and described as examples of different pacing situations and environments in which the present system can be used. Those skilled in the art will realize that the leads can be combined and used in different variations.

Device 170 is a pulse generator such as a bradycardia or antitachycardia pacemaker, a cardioverter, a defibrillator, a combination pacemaker/defibrillator, or other device for providing therapy to a heart or diaphragm. Device 170 is adapted to be subcutaneously implanted in a patient, usually in a pectoral region or an abdominal region. Device 170 includes components that are enclosed in a hermetically sealed can 171. Can 171 includes a can electrode 172.

Device 170 delivers a pulses to heart 101 and/or to phrenic nerves 102 or 103 depending on the placement of the electrodes. For example, FIG. 1B shows an electric pulse 199 being delivered to phrenic nerve 103 from electrode 141 through myocardium 104. The nature of electric pulse 199 will vary from patient to patient depending on the exact location of the electrode. The electric stimulus needed to stimulate either of the phrenic nerve branches 102 or 103 is a function of the position of the implanted electrode. The exact pulse level is determined after insertion of the lead and electrode. It is desirable to keep the pulse level relatively low to conserve battery power and to preserve patient comfort. Thus, the threshold voltage needed to stimulate the phrenic nerve can vary accordingly.

It is contemplated that, considering the factors of electrode position and power conservation, the threshold voltage needed to stimulate the phrenic nerve will be an RMS constant voltage stimulus in the range between 0.2 volts to 14 volts with a pulse duration between approximately 0.2 milliseconds to 12 milliseconds. Alternatively, a physician can choose a constant current pulse having the same approximate energy range. The present system is not limited by the level of the pulse. In the present embodiment, the electric stimulus pulse shape is biphasic. The first phase is cathodic rectangular. The second phase is anodic with an exponential decay. Those skilled in the art will recognize that the actual pulse level must be determined at time of lead insertion and that it and the pulse shape (e.g. triphasic or monophasic) are variable, depending on the physician's desired therapy.

Alternatively, an electrode, such as electrode 141, is implanted so as to help steer the electrical current produced by a device 170 to the phrenic nerve without impacting or capturing heart 101. The methods of inserting or implanting electrode 141 in heart 101 so as to affect certain areas of the heart are known in the art.

Figure 2:
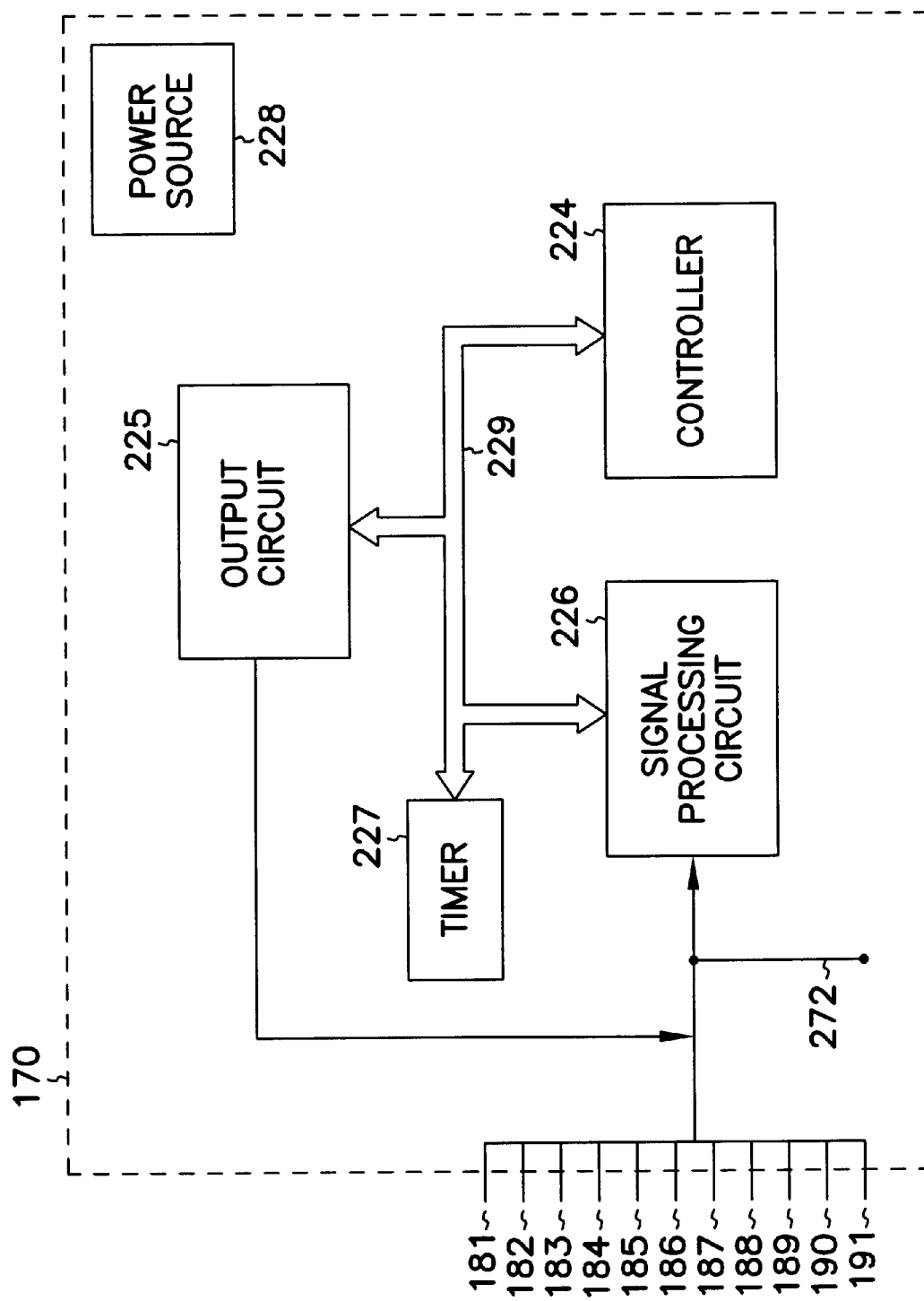
FIG. 2 is a schematic view of parts of a pacing apparatus according to one embodiment of the present system.

FIG. 2 shows a schematic drawing of one embodiment of portions of device 170. In this embodiment, device 170 includes inputs 181–191. However, the present system is not limited by the number of inputs. Inputs 181–191 carry electrical signals from electrodes implanted in or near the heart. Device 170 also includes an input 272 which carries electrical signals from can electrode 172. Inputs 181–191 and 272 are coupled to a signal processing circuit 226. Signal processing circuit 226 is coupled to controller 224. Device 170 also includes a timer 227 coupled to controller 224, and a power source 228. Controller 224 is coupled to output circuit 225, which is coupled to inputs 181–191 for delivering an electric stimulus to a heart or phrenic nerve via a electrode. In one embodiment, the components described above are coupled via a bus 229.

Signal processing circuit 226 is a circuit for receiving, processing and filtering electrical signals sensed by electrodes implanted in a body. Signal processing circuit 226 contains amplifiers and circuits to filter and amplify the electrical signals delivered via a lead. Examples of such signals include signals such as transthoracic impedance or heart activity signals. These signals are representative of a patient's physiological state. For example, if a lead such as lead 130 is inserted into or placed near a heart, signal processing circuit 226 can detect an impedance level between electrode 131 and can electrode 172 and an impedance level between ring electrode 132 and can electrode 172.

One physiological state that can be sensed by signal processing circuit 226 is a patient's minute ventilation. Minute ventilation is a respiratory related parameter that is a measure of the volume of air inhaled and exhaled during a particular period of time. The minute ventilation is the product of respiration rate and tidal volume. In one embodiment, it can be estimated using a bipolar lead such as leads 120, 130, 140, or 150 as shown in FIG. 1A. Minute ventilation can be estimated by frequent measurements of transthoracic impedance between a tip electrode and a pulse generator can electrode when a low energy pulse is delivered from a ring electrode every 50 milliseconds. By measuring the frequency of respiration-related fluctuations in impedance (correlated with respiratory rate) and the amplitude of those excursions (correlated with tidal volume), the estimated minute ventilation can be estimated. Signal processing circuit 226 can also be used to receive and process signals representing other signals representing respiratory activity such as intrathoracic pressure and chest wall motion.

Signal processing circuit 226 also can receive signals representative of heart activity such as native depolarization or fibrillation. By filtering the respiratory activity signals from the heart activity signals, for example by applying a bandpass filtering circuit in the signal processing circuit, the different frequencies of the heart sensing electrogram and the minute ventilation sensing system can be separated, and separately output to controller 224.

Controller 224 includes one or more microprocessors and logic circuits for execution of software or firmware instructions. The software of controller 224 is modifiable to provide different functions. The output of controller 224 depends on the input from signal processing circuit 226. In one embodiment, for example, if the controller determines that a pre-programmed level of respiration has been reached, or that a pre-programmed amount of time has passed, it sends a signal to output circuit 225 to deliver an electric stimulus to phrenic nerve 102 or 103. If controller 224 does not determine a need for therapy it does not deliver the signal. In one embodiment, the controller logic circuit is programmed in a triggered mode, and the controller is programmed to send an output signal to the output circuit when the minute ventilation goes below a predetermined level. When the minute ventilation goes below that level, the controller sends a signal to the output circuit to deliver a pulse to the phrenic nerve via the lead and electrode. The logic circuit of the controller can also be programmed to deliver in an inhibited mode or in an asynchronous mode.

Figure 8:
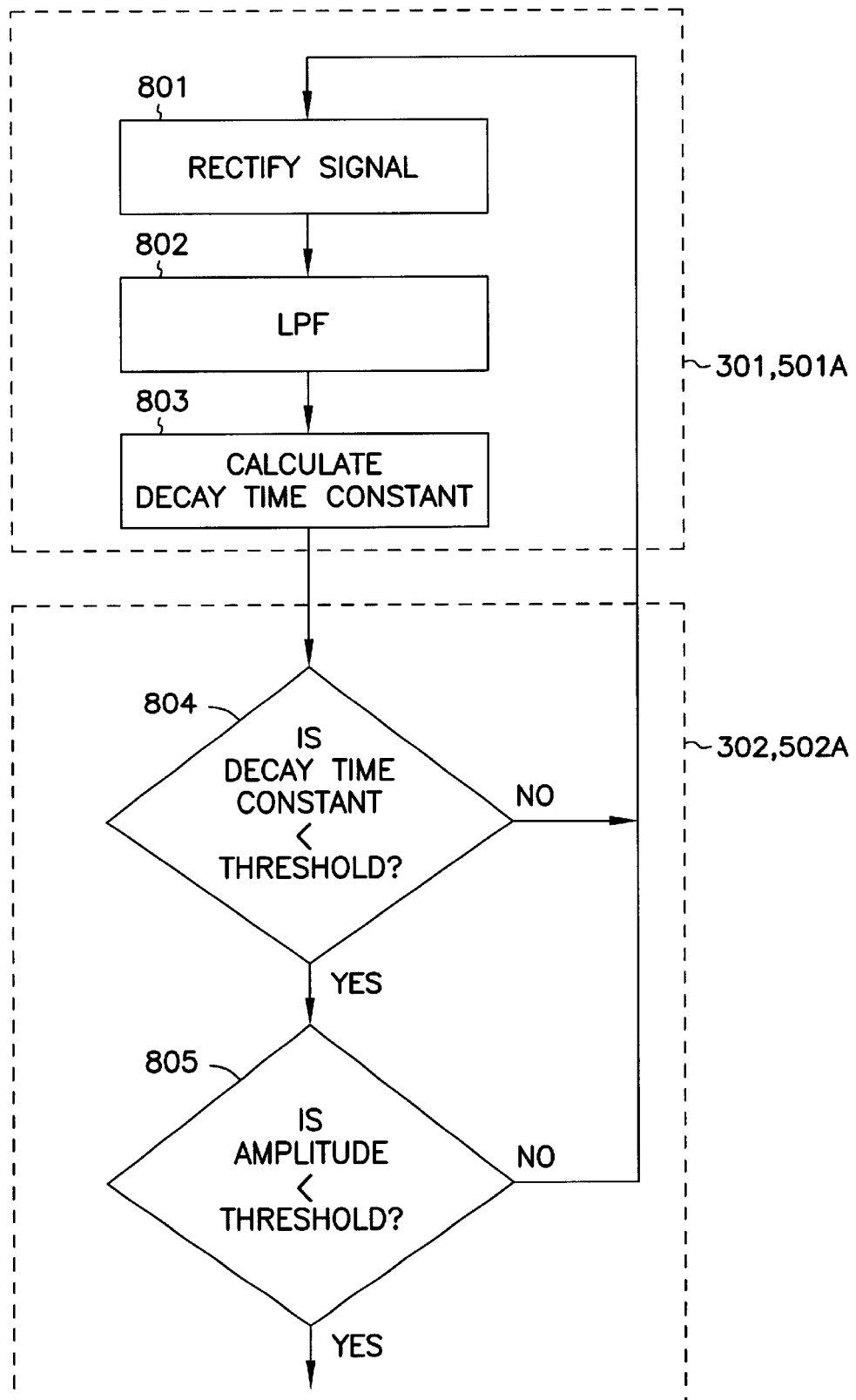
FIG. 8 is a flow chart illustrating a method for performing features of FIGS. 3 and 5.

Controller 224 can also be externally programmed. FIG. 8 shows an exemplary programmable controller system 800. System 800 is known in the art, and it includes an external programmer 801 having a transducer 802, which sends signals to controller 224 and other components in device 170. Using programmable controller system 800, a physician can change the operating mode of device 170 and controller 224. For example, it can be changed from inhibited mode to triggered mode or asynchronous mode. Other details of operating modes will be described below.

EXEMPLARY OPERATION OF THE SYSTEM

Figure 3:
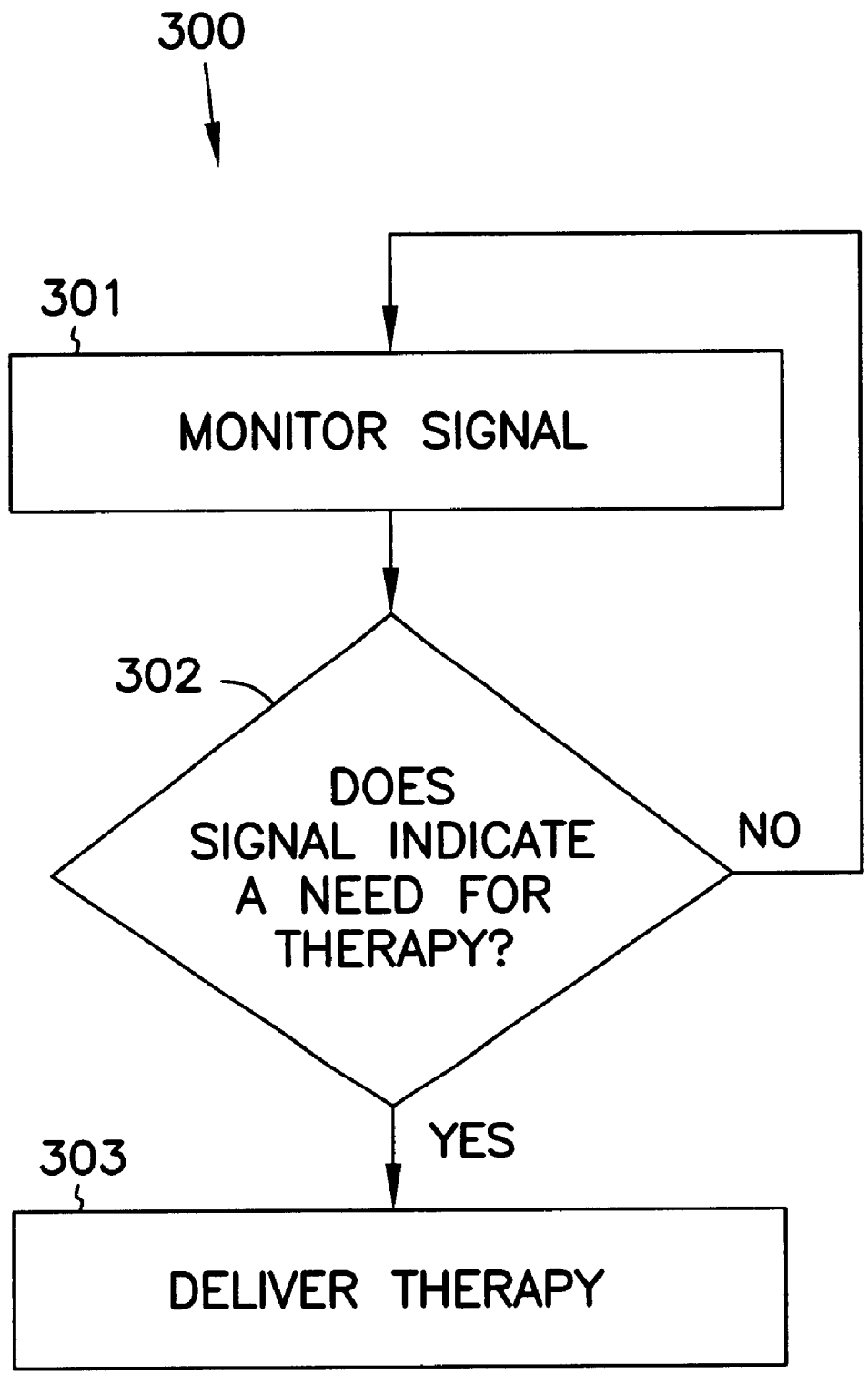
FIG. 3 is a flow chart illustrating a method for diaphragmatic pacing according to one embodiment of the system.

FIG. 3 shows a flowchart illustrating a method of performing diaphragmatic pacing after a lead or leads is inserted into or near a heart as described above. As explained above, the lead position can range from the superior vena cava to either atrium or to either ventricle. Any lead with an electrode capable of stimulating the phrenic nerve will work, such as a bipolar or unipolar cardiac pacing lead, or a defibrillation lead having sensing/pacing electrodes. The lead is inserted into or near the heart in a position to affect the phrenic nerve when an electric stimulus is applied as explained above. FIG. 1A is an exemplary environment in which the present method can be performed, but it is understood that the environment shown in FIG. 1A does not limit the present method.

In FIG. 3, an electrical signal is monitored in block 301. The signal monitored is a sensed and filtered signal input from an electrode. The electrical signal represents a physiological state, such as respiratory activity. The state can be a patient's minute ventilation, for example. Alternatively, it could be chest wall motion.

In block 302, the present system analyzes whether the signal indicates a need for respiratory therapy. The system can be programmed so that the level of respiration which requires therapy is variable. The physician can set the level at what he or she thinks is necessary. For example, if the present system is used to alleviate apnea, block 302 can be set so that if the minute ventilation goes below a preselected apneic threshold set by the physician, such as 5 liters/minute, then the method goes to block 303.

Referring again to FIG. 3, if the analysis in block 302 indicates a need for therapy, a pulse is delivered to the phrenic nerve in block 303. As noted above, the exact pulse level/threshold level for stimulation of the phrenic nerve is determined during implantation, and it is desired to keep the level as low as possible to save battery power and provide patient comfort.

Figure 9:
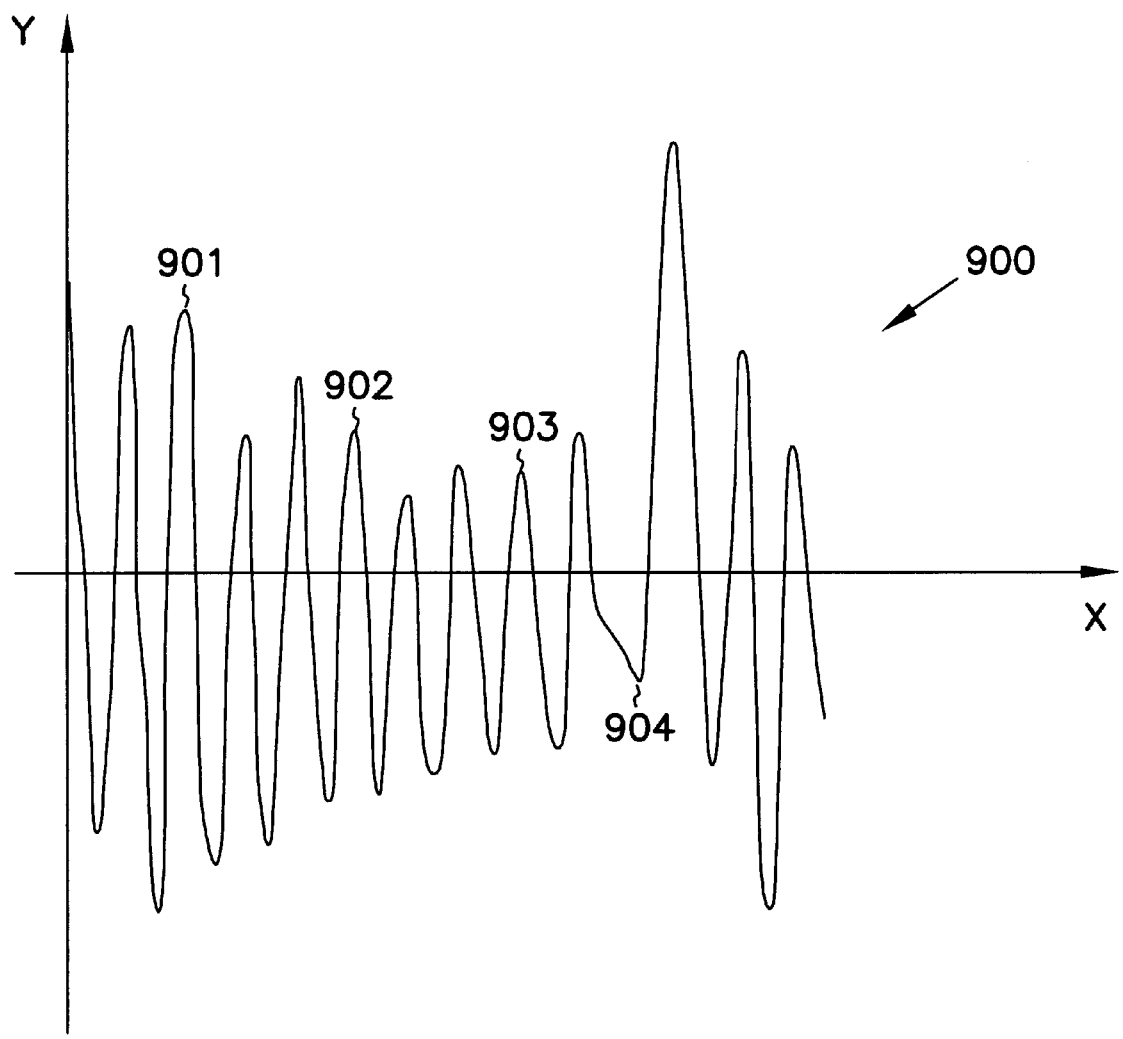
FIG. 9 is a graph representing Cheyne-Stokes respiration in a patient.
Figure 10:
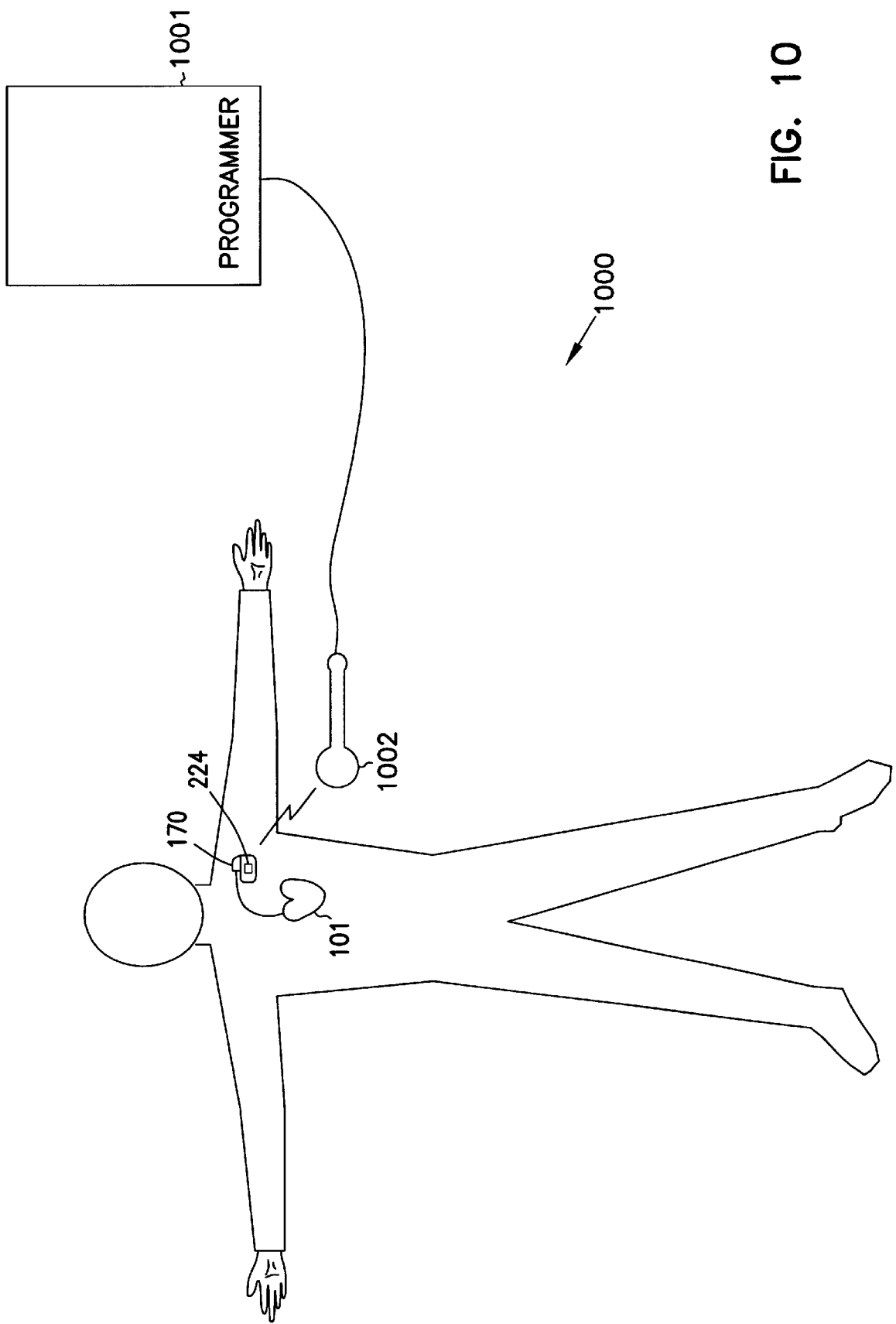
FIG. 10 is a view of an implanted programmable pacing system.

In one embodiment, the method in FIG. 3 is used to provide therapy for Cheyne-Stokes respiration. FIG. 9 shows a graphical representation of a Cheyne-Stokes respiration pattern 900. In FIG. 9, the y-axis is chest wall motion or minute ventilation which represents a tidal volume signal having an amplitude (y). The x-axis represents time. The Cheyne-Stokes respiration pattern 900 signal envelope shrinks over time as shown by the lowering of the amplitude from signal amplitude 901 to signal amplitude 902 to signal amplitude 903. Signal 904 is a brief pause in breathing.

One embodiment of a method to monitor and analyze a Cheyne-Stokes respiration signal in blocks 301 and 302 is illustrated in FIG. 8. In FIG. 8, the monitoring and analyzing done in FIG. 3, blocks 301 and 302, includes rectifying the signal in block 801. In block 802, the signal is low pass filtered (LPF). In block 803, the decay time constant of the signal is calculated. In block 804, the method analyzes whether the decay time constant calculated in block 803 is below a preset threshold level determined by a physician. If the answer is positive, the method determines, in block 805, whether the signal amplitude is below a preset threshold determined by a physician. If the answer is positive then the method delivers the therapy in block 303.

Figure 4:
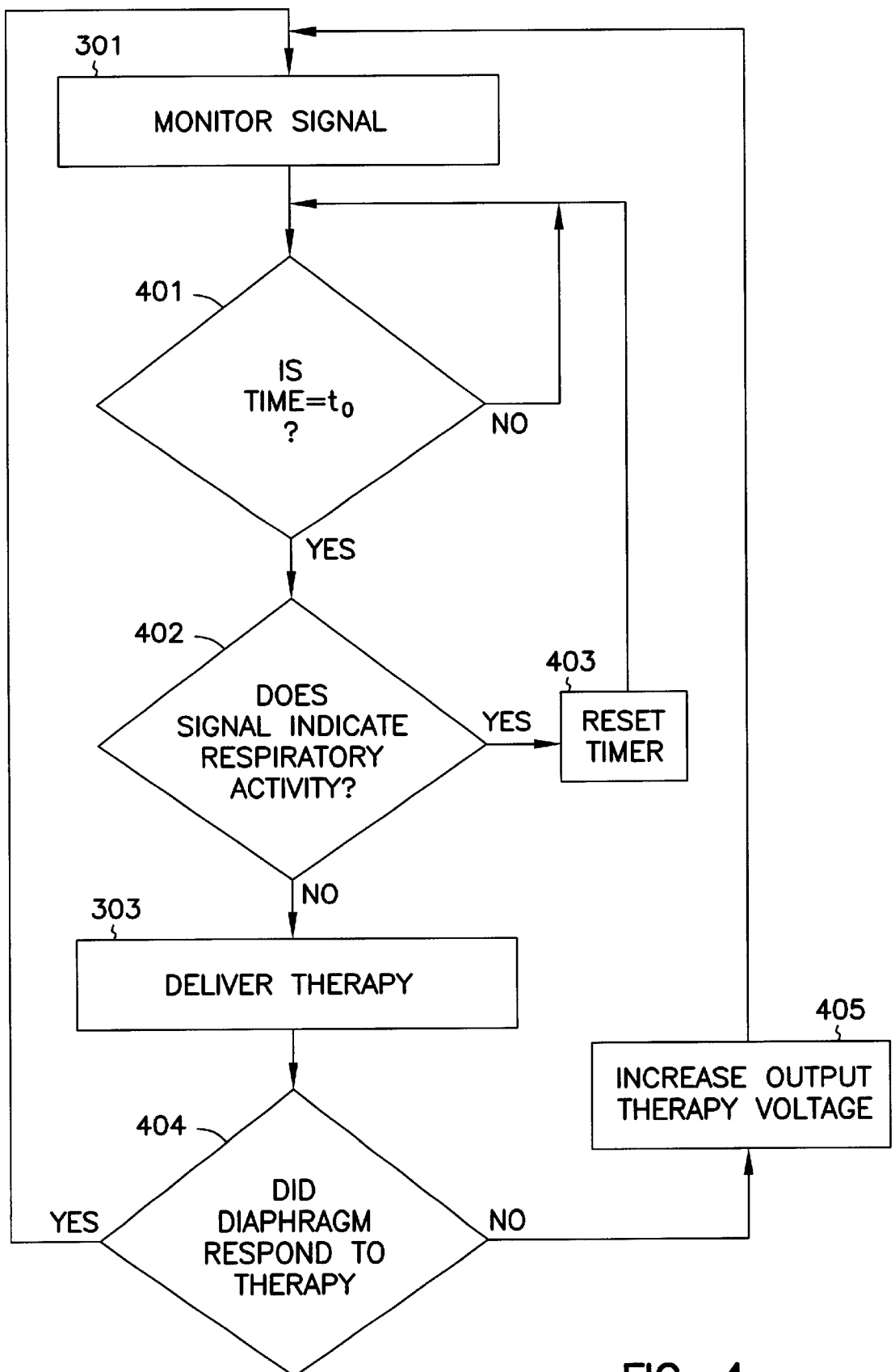
FIG. 4 is a flow chart illustrating another method for diaphragmatic pacing according to one embodiment of the system.

FIG. 4 shows an exemplary method for performing diaphragmatic pacing in an inhibited mode. The method illustrated in FIG. 4 is similar in part to the method illustrated in FIG. 3, and like blocks are indicated by the like numbers. By way of example, but not limitation, the method illustrated in FIG. 4 can be used in a system incorporating a lead such as leads 120, 140, 150, or 160 in FIG. 1A.

Referring to FIG. 4, in block 301 a signal is monitored. In block 401 a timer is analyzed. The timer of the present method can be programmed or set to deliver any breathing rate or frequency required or desired by a physician, such as 10, 20, or 40 breaths per minute, for example. If the time analyzed in block 401 is equal to the preset time, then the method goes to block 402. In block 402, the method analyzes whether the signal from block 301 indicates the preset level of respiratory activity. If the signal does indicate that the respiratory level is sufficient, the timer is reset in block 403 and the method returns to block 401. If the signal analyzed in block 402 does not indicate that the respiratory level is sufficient, the method goes to block 303 and the therapy is delivered. In block 404, the present method analyzes whether the diaphragm responded to the therapy delivered in block 303. This can be done by analyzing the signal representing respiratory activity shortly after the therapy is delivered. If it is determined in block 404 that the diaphragm did not respond to the therapy, then the voltage pulse level is increased in block 405. The method illustrated in FIG. 4 delivers the stimulation pulse at a predetermined frequency unless the input signal indicates that the minute ventilation is above a predetermined level. The electric stimulus is delivered by the output circuit via the lead to the electrode to the phrenic nerve.

In one embodiment, the method shown in FIG. 4 can be varied to deliver therapy in an asynchronous mode. In such a mode, only time is analyzed (e.g. the method would not contain block 402, or block 402 could be programmed to always return a negative result). An asynchronous mode can be useful if a patient has paralysis or other problem in which they cannot breath on their own.

Figure 5:
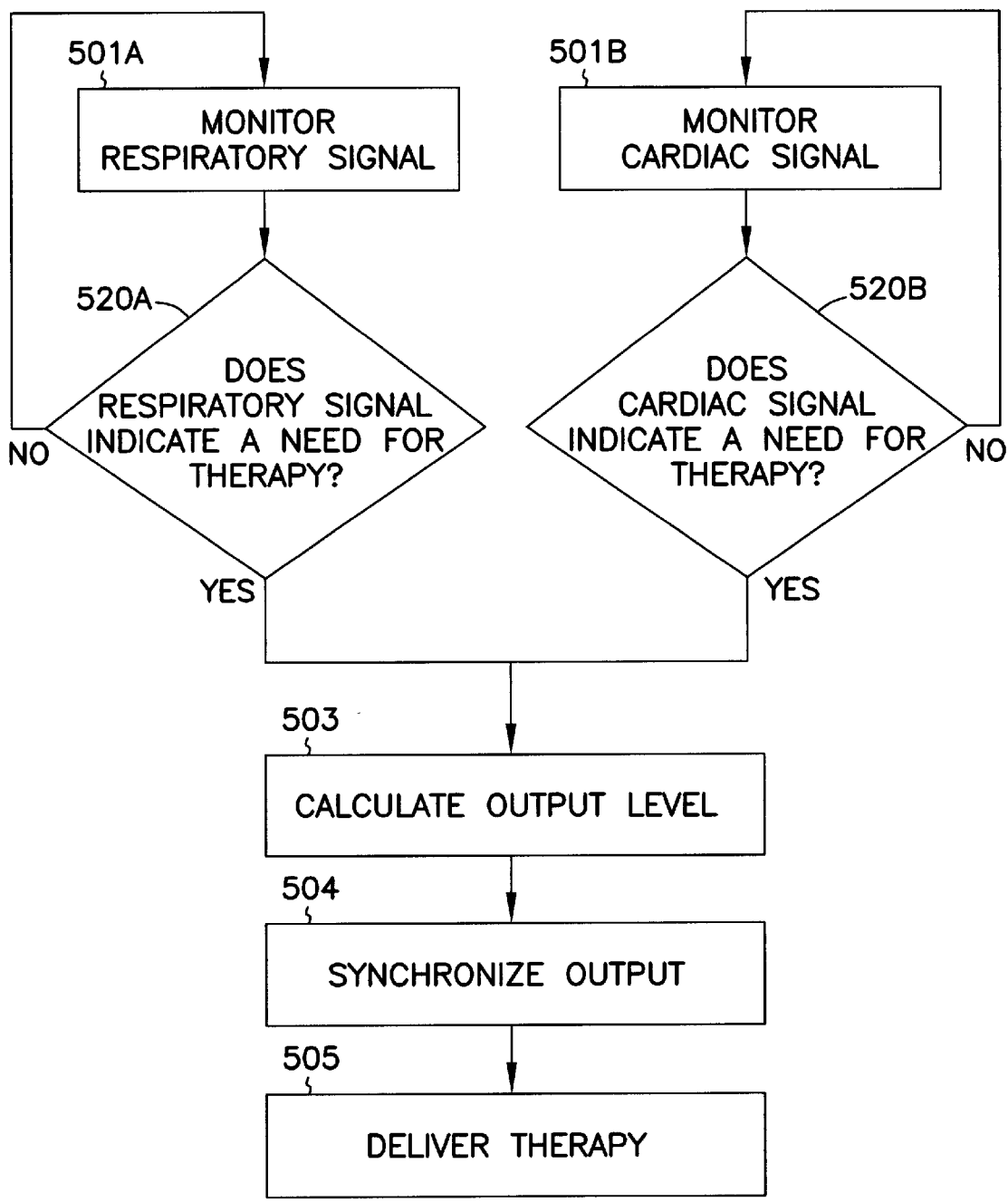
FIG. 5 is a flow chart illustrating a method for heart and diaphragmatic pacing according to another embodiment the system.

FIG. 5 shows an exemplary method for sensing and controlling concurrent heart pacing and diaphragmatic pacing or concurrent diaphragmatic pacing and heart defibrillation. The inserted leads can be a pacing lead or a defibrillation lead. Exemplary leads include leads such as lead 140 in FIG. 1A, or a combination of leads such as leads 120 and 130 or leads 130 and 150.

In block 501A, a first signal indicative of respiratory activity is monitored, such as a signal representing minute ventilation or chest wall motion as described above. Concurrently, in block 501B a second signal indicative of heart activity (sensing for native depolarization, for example) is monitored. As noted above, by filtering the signals, for example by applying a bandpass filtering circuit in the sensor circuit, the different frequencies of the cardiac sensing electrogram and the minute ventilation sensing system can be separated, and separately output to the controller.

In block 502A, the method analyzes whether the signal monitored in block 501A indicates a need for respiratory therapy. The system can be programmed so that the level of respiration which requires therapy is variable. The physician can set the level at what he or she thinks is necessary. For example, if the present system is used to alleviate apnea, block 502A can be set so that if the minute ventilation goes below a preselected apneic threshold set by the physician, such as 5 liters/minute, then the method goes to block 503. Alternatively, if the method illustrated in FIG. 5 is used to provide therapy for a patient suffering from Cheyne-Stokes respiration, a method such as illustrated in FIG. 8 can be used.

In block 502B the method analyzes whether the heart activity signal monitored in block 501B indicates a need for therapy. Alternatively, the method in block 502B could be in an inhibited mode analogous to block 401 and 402 of the method of FIG. 4. The analysis of block 502B can be done concurrently or independently from the analysis of block 502A.

Figure 6:
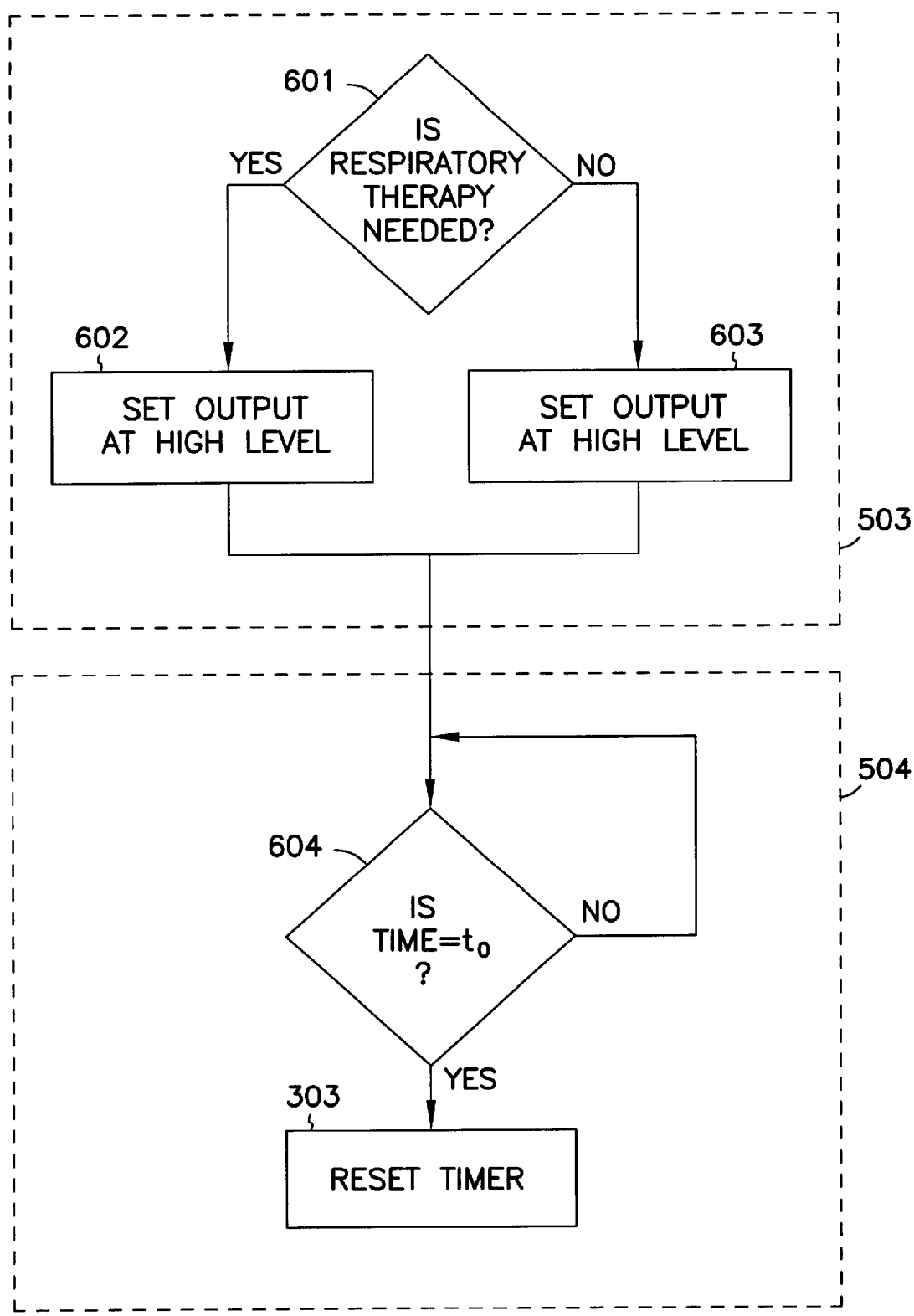
FIG. 6 is a flow chart illustrating a method for performing features of FIG. 5.

If either block 502A or 502B indicate a need for therapy, the method goes to block 503, which calculates the necessary output level. One embodiment of a method to calculate the necessary output level in block 503 is illustrated in FIG. 6. In FIG. 6, the method analyzes, in block 601, whether respiratory therapy was needed as indicated from block 502A. If, in block 601, the method finds that respiratory therapy was not needed as indicated from block 502A, then in block 603 the output level is set to a low output level, $P_1$. By way of example, but not limitation, a low output level can be $P_1=0.5$ volts. $P_1$ is delivered when only the heart pacing therapy is required. $P_1$ is a pulse which is high enough to stimulate the heart but not high enough to cause the diaphragm to be stimulated. It is contemplated that a pulse in the RMS constant volt range 0.1 volts to 5 volts at a duration of 0.1 milliseconds to 2 milliseconds will be satisfactory. The important thing during testing of this threshold level is that the heart alone and not the diaphragm should be stimulated.

If, in block 601, the method finds that respiratory therapy was needed as indicated from block 502A, then in block 602 the output level is set to a high setting, $P_2$. By way of example, but not limitation, a high output level can be $P_2=3$ volts. $P_2$ is in a range approximately twice the amplitude of $P_1$, although the exact level is not determined until the threshold is determined during testing after implantation. It is contemplated that $P_2$ will be an RMS constant voltage pulse of approximately 0.2 volts to 14 volts with a duration of 0.2 milliseconds to 12 milliseconds. Again, the important thing is that the pulse stimulates both the diaphragm via the phrenic nerve and the heart. Although the contemplated ranges of voltages described above for $P_1$ and $P_2$ overlap, the implanting physician can test the results of different pulses until a satisfactory gap is discovered between them. In other words, the precise level of $P_1$ and $P_2$ is not meant to limit the present system. For example, the physician may discover that the heart needs a minimum voltage of 1.5 volts to be stimulated while the diaphragm needs a minimum of 3 volts. The physician can set $P_1$ to approximately 1.5–2.0 volts and $P_2$ to approximately 3.5 volts.

Since the heart rate is higher than the respiratory rate, the pacing rate of $P_1$ may be faster than the pacing rate of $P_2$. An example would be if the required heart rate were 70 beats per minute and the breathing rate were 10 or 20 breaths per minute. In block 504, the method illustrated in FIG. 5 synchronizes the output pulse. In FIG. 6, one embodiment of a method to synchronize the output pulse is illustrated. In block 604, the method analyzes whether a preset amount of time has passed. If not, the method continuously loops until the preset time is reached. Once the time is reached, the method resets the timer and delivers the pulse in block 505. A physician can set the time parameter used in block 604 to optimize different therapeutical situations. For example, it can be set so that a pulse $P_1$ for pacing the diaphragm is delivered at the same time that the heart would be paced if it needed to be. Since $P_2$ also delivers heart therapy, the two therapies do not conflict. Alternatively, pulse $P_1$ can be delivered during the refractory period of a heart beat. The output algorithm pattern would keep the heart rate steady and adjust $P_2$ to match when a $P_1$ is called for so that the two pulses do not conflict with each other.

In another embodiment of the method (not shown), the diaphragm therapy pulse, $P_2$, is delivered in a triggered mode as described above, while the heart therapy pulse, $P_1$, is delivered in inhibited mode as described for FIG. 4. When the method triggers a $P_2$ pulse, it would deliver the $P_2$ pulse at a same point in time as a $P_1$ would be delivered, thus, the two pulses wouldn't conflict with each other. Another embodiment of the method is to deliver $P_2$ during the refractory period of the cardiac tissue.

In one embodiment of the method illustrated in FIG. 5, the method can include features such as analyzing whether the diaphragm responded to the therapy. An example of such analysis is illustrated in blocks 404 and 405 of the method of FIG. 4. Those skilled in the art will recognize that this and other combinations and permutations of the present system are possible and the examples given are to be considered exemplary and not limiting.

Figure 7:
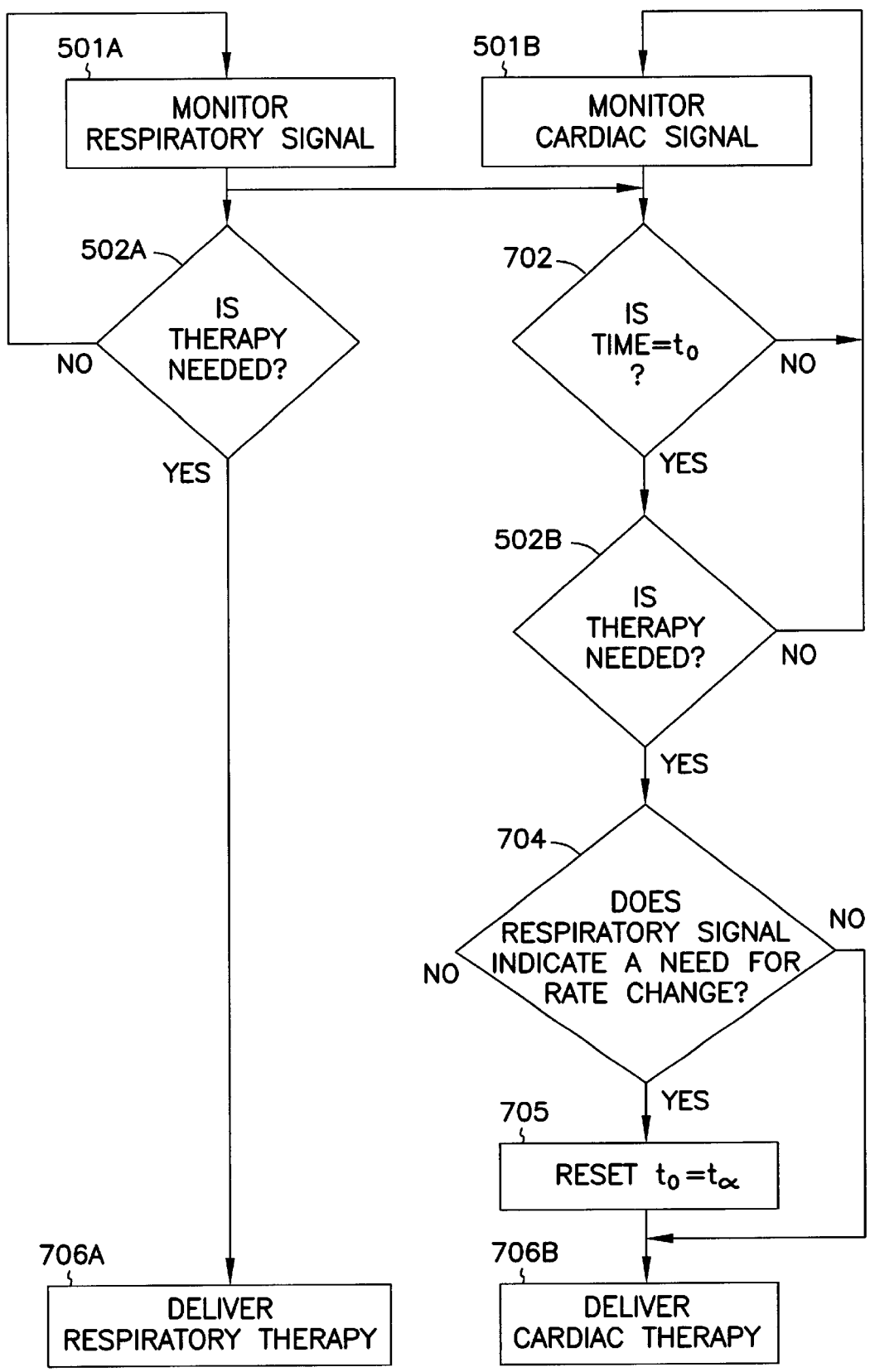
FIG. 7 is a flow chart illustrating another method for heart and diaphragmatic pacing according to another embodiment of the system.

FIG. 7 is a flow chart of an exemplary method for performing concurrent, yet independent, heart and diaphragmatic pacing from a single implanted pulse generator device according to another embodiment of the system. Doing both types of pacing from one device creates less risk of failure than doing it from two separate implanted devices. Also, by implanting a single device the patient only needs one implantation operation instead of two, which also lessens the risk of complications.

In this embodiment of the system, a first pacing lead is inserted in the heart positioned so that the phrenic nerve alone is affected by an electric stimulation and the heart is not affected by it. One method to accomplish this is to place the electrode in superior vena cava 110, as exemplified by lead. 120 in FIG. 1A. Such lead placement permits the phrenic nerve 102 to be stimulated without stimulating heart 101. Another method to accomplish this is using field steering. For example, a lead such as lead 140 or 150 can be positioned so that the stimulus is directed only to can electrode 172 and the phrenic nerve alone is affected. A second pacing or defibrillation lead is inserted to perform cardiac pacing or defibrillation, the two systems running concurrently and independently from a single pulse generator device. Examples of such environments include leads 130, 140, or 160.

The method illustrated in FIG. 7 is similar in part to the method illustrated in FIG. 5, and like blocks are indicated by the like numbers. In block 501A, a first signal indicative of respiratory activity is monitored, such as a signal representing minute ventilation or chest wall motion as described above. In block 501B a second signal indicative of heart activity (sensing for native depolarization, for example) is monitored.

In block 502A, the method analyzes whether the signal monitored in block 501A indicates a need for respiratory therapy. The system can be programmed so that the level of respiration which requires therapy is variable. The physician can set the level at what he or she thinks is necessary. In block 702 the method analyzes whether a preset amount of time has passed. If it has the method goes to block 502B. In block 502B, the method analyzes whether the heart activity signal monitored in block 501B indicates a need for therapy. Alternatively, the method in block 502B could be in a triggered mode, and the method would not include block 702.

In one embodiment of the method illustrated in FIG. 7, the minute ventilation information monitored in block 501A is used in blocks 704 and 705 to vary the rate of the cardiac pacing pulse, as is known in the art. This is possible because the minute ventilation rate is related to bodily activity and if it rises it indicates a need for a faster heart pacing rate.

The respective diaphragm and heart therapies are delivered either concurrently or independently in blocks 706A and 706B. Since the output of each lead is independent (the heart therapy does not affect the phrenic nerve and vice versa), the method does not have to synchronize the output therapy pulses as detailed for the methods described above because each pulse does not effect the other's function.

Some of the advantages of the present system are that it provides diaphragmatic pacing using the advanced, developed technology provided by modern cardiac pacing lead technology. Diaphragmatic pacing from a pacing lead will not cause nerve damage compared to nerve cuffs, which are directly attached to the phrenic nerve. Since cardiac pacing has been done since the 1950's, pacing leads are well developed, well tested, and reliable. Furthermore, intravenously implanting pacing leads is less invasive than attaching a nerve cuff to a phrenic nerve. It also provides phrenic pacing without the invasive surgery associated with attaching nerve cuffs. Furthermore, it provides a physician the option of doing concurrent heart pacing and diaphragm pacing using one implanted system instead of two.

What is claimed is:

1. A method, comprising:
   delivering an electric stimulus from a lead situated within a body to a phrenic nerve at a controlled rate, wherein the electric stimulus is delivered in a region proximate a wall of a heart, wherein the electric stimulus is delivered from an electrode on the lead, the electrode being located on or within the heart.

2. The method of claim 1, wherein the lead comprises a cardiac rhythm management lead.

3. The method of claim 1, wherein the controlled rate is determined by analyzing whether a signal representing a respiratory state indicates a need for the electrical stimulus.

4. A method, comprising:

delivering an electric stimulus from a lead situated within a body to a phrenic nerve at a controlled rate, wherein the electric stimulus is delivered in a region proximate a wall of a heart, wherein the lead is situated along a lateral wall of a heart.

5. The method of claim 4, wherein the lead comprises: a cardiac rhythm management lead.

6. The method of claim 4, wherein the controlled rate is determined by a method comprising:

analyzing whether a signal representing a respiratory state indicates a need for the electrical stimulus.

7. The method of claim 6, wherein the respiratory state is a patient's chest wall motion.

8. A method, comprising:

delivering an electric stimulus from a lead situated within a body to a phrenic nerve at a controlled rate, wherein the electric stimulus is delivered in a region proximate a wall of a heart, wherein the controlled rate is a asynchronous mode rate.

9. A method, comprising:

delivering an electric stimulus from a lead situated within a body to a phrenic nerve at a controlled rate, the electric stimulus being delivered in a region proximate a wall of a heart, wherein the controlled rate is determined by analyzing whether a signal representing a patient's minute ventilation indicates a need for the electrical stimulus.

10. A method, comprising:

monitoring a signal representing a patient's respiratory activity; and delivering an electric stimulus from a lead to a phrenic nerve when the signal indicates that the respiratory activity is below a predetermined level, wherein the electric stimulus is delivered in a region proximate to where the phrenic nerve runs along a wall of a heart of the patient.

11. The method of claim 10, wherein the lead is situated in a superior vena cava.

12. The method of claim 10, wherein the lead is situated along a lateral wall of a heart.

13. The method of claim 10, wherein monitoring a signal comprises:

rectifying the signal;

applying a low pass filter to the signal; and calculating a decay time constant of the signal.

14. The method of claim 13, further comprising analyzing whether the decay time constant is below a preset level; and analyzing whether an amplitude of the signal is below a preset level.

15. The method of claim 10, wherein the respiratory activity comprises a chest wall motion.

16. The method of claim 10, wherein the respiratory activity comprises a minute ventilation.

17. The method of claim 10, further comprising increasing the amplitude of the electric stimulus if the respiratory activity does not increase after the electric stimulus has been delivered.

18. A method for pacing a heart and a diaphragm, comprising:

analyzing a first signal which indicates whether the heart needs pacing and analyzing a second signal which indicates whether the diaphragm needs pacing;

delivering a first electric stimulus at a first controlled rate to pace the heart when the first signal indicates a need for heart pacing; and delivering a second electric stimulus at a second controlled rate to pace the diaphragm when the second signal indicates a need for diaphragmatic pacing.

19. The method of claim 18, wherein delivery is from a single pulse generator.

20. The method of claim 18, wherein the first electric stimulus is at a level higher than a heart pacing threshold and lower than a diaphragm pacing threshold, and the second electric stimulus is higher than a diaphragm pacing threshold.

21. The method of claim 18, wherein the first electric stimulus and the second electric stimulus are delivered from the same lead as each other.

22. The method of claim 21, further comprising synchronizing the delivery of the first electric stimulus and the second electric stimulus.

23. A method for heart and diaphragmatic pacing, comprising:

monitoring a first signal representing a patient's respiratory activity;

monitoring a second signal representing a patient's heart activity;

delivering a first electric stimulus to the phrenic nerve at a first controlled rate when the signal indicates that the respiratory activity is below a predetermined level; and delivering a second electric stimulus to the heart at a second controlled rate when the signal indicates that the heart activity is below a predetermined level.

24. The method of claim 23, wherein the first electric stimulus is delivered using field steering.

25. The method of claim 23, wherein the first electric stimulus is in the constant voltage range 0.2 volts to 14 volts at a duration of 0.2 to 12 milliseconds, and the second stimulus is in the constant voltage range 0.1 volts to 4 volts at a duration of 0.1 to 2 milliseconds.

26. The method of claim 23, further comprising increasing the amplitude of the first electric stimulus if the respiratory activity does not increase after the first electric stimulus has been delivered.

27. A system, comprising:

at least one lead having a plurality of electrodes;

a signal processing circuit coupled to each of the at least one leads, the signal processing circuit processes a signal representative of a respiratory activity;

a controller coupled to the signal processing circuit, the controller analyzes the signal, when the signal indicates a need for respiratory therapy the controller outputs a controller signal; and an output circuit coupled to the controller, the output circuit delivers a pulse in response to the controller signal, the pulse having an amplitude high enough to stimulate a phrenic nerve, wherein the pulse is in the constant voltage range 0.2 volts to 14 volts at a duration of approximately 0.2 to 12 milliseconds.

28. The system of claim 27, wherein the lead comprises a cardiac rhythm management lead.

29. The system of claim 27, wherein the controller increases the amplitude of the pulse if the respiratory activity does not increase after the pulse has been delivered.

30. The system of claim 27, wherein the signal processing circuit comprises:

a rectifying circuit for rectifying the signal;

a low pass filter circuit for applying a low pass filter to the signal; and a circuit for calculating a decay time constant of the signal.

31. The system of claim 30, wherein the controller comprises:

a means for analyzing whether the decay time constant is below a preset level; and a means for analyzing whether an amplitude of the signal is below a preset level.

32. A system, comprising:

at least one lead having a plurality of electrodes;

a signal processing circuit coupled to each of the at least one leads, the signal processing circuit processes a first signal representative of a respiratory activity, the signal processing circuit senses a second signal representative of a cardiac activity;

a controller coupled to the signal processing circuit, the controller analyzes the first signal and the second signal, when the first signal indicates a need for respiratory therapy the controller outputs a first controller signal, when the first signal does not indicate a need for respiratory therapy and the second signal indicates a need for cardiac therapy the controller outputs a second controller signal; and an output circuit coupled to the controller, the output circuit delivers a first pulse in response to the first controller signal, the first pulse having an amplitude high enough to stimulate a phrenic nerve, the output circuit delivers a second pulse in response to the second controller signal, the second pulse having an amplitude high enough to pace a heart but not high enough to stimulate a phrenic nerve.

33. The system of claim 32, wherein when the controller outputs a second signal, the controller output rate is dependent on the first signal representative of a patient's respiratory activity.

34. A method for heart and diaphragmatic pacing, comprising:

monitoring a first signal representing a patient's respiratory activity;

monitoring a second signal representing a patient's heart activity;

delivering a first electric stimulus to a phrenic nerve at a first controlled rate when the first signal indicates that the patient's respiratory activity is below a predetermined level; and delivering a second electric stimulus to a heart at a second controlled rate when the second signal indicates that the patient's heart activity is below a predetermined level, wherein the first electric stimulus is in the constant voltage range 0.2 volts to 14 volts at a duration of 0.2 to 12 milliseconds, and the second stimulus is in the constant voltage range 0.1 volts to 4 volts at a duration of 0.1 to 2 milliseconds.

35. The method of claim 34, wherein the first electric stimulus is delivered using field steering.

36. The method of claim 34, further comprising increasing the amplitude of the first electric stimulus if the respiratory activity does not increase after the first electric stimulus has been delivered.

* * * * *